US011317923B2

(12) United States Patent
Thomas et al.

(10) Patent No.: US 11,317,923 B2
(45) Date of Patent: May 3, 2022

(54) LIGATION CLIP WITH IMPROVED HINGE (71) Applicant: Covidien LP, Mansfield, MA (US)

(72) Inventors: Justin Thomas, New Haven, CT (US); Eric Brown, Haddam, CT (US); Jacob C. Baril, Norwalk, CT (US); Gregory R. Morck, Middletown, CT (US); Roy J. Pilletere, North Haven, CT (US); Saumya Banerjee, Hamden, CT (US); Matthew A. Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 225 days.

(21) Appl. No.: 16/432,984

(22) Filed: Jun. 6, 2019

(65) Prior Publication Data
US 2020/0046359 A1 Feb. 13, 2020

Related U.S. Application Data (60) Provisional application No. 62/717,958, filed on Aug. 13, 2018.

(51) Int. Cl.
*A61B 17/122* (2006.01)
*A61B 17/12* (2006.01)

(52) U.S. Cl.
CPC .. *A61B 17/122* (2013.01); *A61B 2017/12004* (2013.01)

(58) Field of Classification Search
CPC . A61B 17/122; A61B 17/083; A61B 17/1227; A61B 17/1285; A61B 17/0487;
(Continued)

(56) References Cited

U.S. PATENT DOCUMENTS

| 3,439,523 A | 4/1969 | Wood |
| 3,713,533 A | 1/1973 | Reimels |

(Continued)

FOREIGN PATENT DOCUMENTS

| BE | 654195 A | 2/1965 |
| CN | 103919589 A * | 7/2014 |

(Continued)

OTHER PUBLICATIONS

European Search Report dated Dec. 13, 2019, issued in EP Appln. No. 19191228, 13 pages.

(Continued)

*Primary Examiner* — Kelly J Bekker
*Assistant Examiner* — Paige A Codrington
(74) *Attorney, Agent, or Firm* — Carter, DeLuca & Farrell LLP (57) ABSTRACT

A ligation clip includes a first jaw, a second jaw, and a hinge. The first jaw has a body having an inner surface defining a first clamping surface and an outer surface. The second jaw has a body having an inner surface defining a second clamping surface and an outer surface. The hinge is integrally formed with the first and second jaws and includes an inner hinge portion and an outer hinge portion. The inner hinge portion has an inner surface that is contiguous with the first and second clamping surfaces of the first and second jaws, and an outer surface. The inner surface of the inner hinge portion is defined by a plurality of curved sections. The hinge is configured to facilitate pivotal movement of the first jaw in relation to the second jaw between an open position and a clamped position.

17 Claims, 5 Drawing Sheets

(58) Field of Classification Search
CPC ........ A61B 17/282; A61B 2017/12004; A61B 2017/2926; A61B 2017/00584; B65D 33/1675
USPC ...................................................... 606/158
See application file for complete search history.

(56) References Cited

U.S. PATENT DOCUMENTS

| | | | |
|---|---|---|---|
| 4,076,120 A | 2/1978 | Carroll et al. | |
| 4,146,130 A | 3/1979 | Samuels et al. | |
| 4,187,712 A | 2/1980 | Samuels et al. | |
| 4,212,303 A | 7/1980 | Nolan | |
| 4,212,390 A | 7/1980 | Raczkowski et al. | |
| 4,294,355 A | 10/1981 | Jewusiak et al. | |
| 4,344,531 A | 8/1982 | Giersch | |
| 4,346,869 A | 8/1982 | MacNeill | |
| 4,361,229 A | 11/1982 | Mericle | |
| 4,390,019 A | 6/1983 | LeVeen et al. | |
| 4,412,617 A | 11/1983 | Cerwin | |
| 4,418,694 A | 12/1983 | Beroff et al. | |
| 4,449,531 A | 5/1984 | Cerwin et al. | |
| 4,485,953 A | 12/1984 | Rothfuss | |
| 4,487,205 A | 12/1984 | Di Giovanni et al. | |
| 4,550,729 A | 11/1985 | Cerwin et al. | |
| 4,696,396 A | 9/1987 | Samuels | |
| 4,726,372 A | 2/1988 | Perlin | |
| 4,834,096 A | 5/1989 | Oh et al. | |
| 4,936,447 A | 6/1990 | Peiffer | |
| 4,942,886 A | 7/1990 | Timmons | |
| 4,961,499 A | 10/1990 | Kulp | |
| 4,971,198 A | 11/1990 | Mericle | |
| 4,972,949 A | 11/1990 | Peiffer | |
| 5,046,611 A | 9/1991 | Oh | |
| 5,046,624 A | 9/1991 | Murphy et al. | |
| 5,050,272 A | 9/1991 | Robinson et al. | |
| 5,062,846 A | 11/1991 | Oh et al. | |
| 5,100,416 A | 3/1992 | Oh et al. | |
| 5,201,416 A | 4/1993 | Taylor | |
| 5,279,416 A | 1/1994 | Malec et al. | |
| 5,423,831 A | 6/1995 | Nates | |
| 5,564,262 A | 10/1996 | Bevis et al. | |
| 5,634,930 A | 6/1997 | Thornton et al. | |
| 5,676,676 A | 10/1997 | Porter | |
| 5,697,942 A | 12/1997 | Palti | |
| 5,713,912 A | 2/1998 | Porter | |
| 5,846,255 A | 12/1998 | Casey | |
| 5,908,430 A | 6/1999 | Appleby | |
| 5,921,991 A | 7/1999 | Whitehead et al. | |
| 6,044,971 A | 4/2000 | Esposito et al. | |
| 6,158,583 A | 12/2000 | Forster | |
| 6,217,590 B1 | 4/2001 | Levinson | |
| 6,228,097 B1 | 5/2001 | Levinson et al. | |
| 6,273,253 B1 | 8/2001 | Forster et al. | |
| 6,306,150 B1 | 10/2001 | Levinson | |
| 6,349,727 B1 | 2/2002 | Stewart, Jr. | |
| 6,391,035 B1 | 5/2002 | Appleby et al. | |
| 6,419,682 B1 | 7/2002 | Appleby et al. | |
| 6,421,920 B1 | 7/2002 | Jensen | |
| 6,439,727 B1 | 8/2002 | Koide | |
| 6,460,700 B2 | 10/2002 | Weisshaupt | |
| 6,460,749 B2 | 10/2002 | Levinson et al. | |
| 6,780,195 B2 | 8/2004 | Porat | |
| 6,824,547 B2 | 11/2004 | Wilson, Jr. et al. | |
| 6,863,675 B2 | 3/2005 | Wilson, Jr. | |
| 6,880,699 B2 | 4/2005 | Gallagher | |
| 7,001,412 B2 | 2/2006 | Gallagher et al. | |
| 7,052,504 B2 | 5/2006 | Hughett | |
| 7,131,977 B2 | 11/2006 | Fowler | |
| 7,144,402 B2 | 12/2006 | Kuester, III | |
| 7,211,091 B2 | 5/2007 | Fowler et al. | |
| 7,211,092 B2 | 5/2007 | Hughett | |
| 7,316,696 B2 | 1/2008 | Wilson, Jr. et al. | |
| 7,326,223 B2 | 2/2008 | Wilson, Jr. | |
| 7,452,368 B2 | 11/2008 | Liberatore et al. | |
| 7,585,304 B2 | 9/2009 | Hughett | |
| 7,628,272 B2 | 12/2009 | Wiedenbein | |
| 7,857,129 B2 | 12/2010 | Iaconi-Forrer et al. | |
| 8,042,687 B2 | 10/2011 | Cannady | |
| 8,312,992 B2 | 11/2012 | Disch | |
| 8,403,138 B2 | 3/2013 | Weisshaupt et al. | |
| 8,425,515 B2 | 4/2013 | Gamache et al. | |
| 8,627,955 B2 | 1/2014 | Weisshaupt et al. | |
| 8,839,954 B2 | 9/2014 | Disch | |
| 8,888,398 B2 | 11/2014 | Werth | |
| 9,220,507 B1* | 12/2015 | Patel | A61B 17/064 |
| 9,271,737 B2 | 3/2016 | Castro et al. | |
| 9,282,972 B1* | 3/2016 | Patel | A61B 17/1227 |
| 9,445,820 B2 | 9/2016 | Whiting | |
| 9,456,824 B2 | 10/2016 | Willett et al. | |
| 9,480,480 B2 | 11/2016 | Santilli et al. | |
| 9,486,225 B2 | 11/2016 | Michler et al. | |
| 9,517,178 B2 | 12/2016 | Chancibot | |
| D808,522 S | 1/2018 | Cannady et al. | |
| 9,855,053 B2 | 1/2018 | Bagaoisan et al. | |
| 10,130,373 B2 | 11/2018 | Castro et al. | |
| 10,136,898 B2 | 11/2018 | Schmidt et al. | |
| 2002/0046961 A1 | 4/2002 | Levinson et al. | |
| 2002/0177863 A1 | 11/2002 | Mandel et al. | |
| 2004/0044352 A1* | 3/2004 | Fowler | A61B 17/128 606/142 |
| 2004/0199178 A1 | 10/2004 | Small | |
| 2005/0165422 A1* | 7/2005 | Wilson | A61B 17/1222 606/151 |
| 2005/0165423 A1 | 7/2005 | Gallagher et al. | |
| 2005/0165424 A1* | 7/2005 | Gallagher | A61B 17/0487 606/151 |
| 2006/0089659 A1 | 4/2006 | Small | |
| 2006/0124485 A1 | 6/2006 | Kennedy | |
| 2006/0217749 A1 | 9/2006 | Wilson et al. | |
| 2007/0083218 A1 | 4/2007 | Morris | |
| 2007/0118161 A1 | 5/2007 | Kennedy et al. | |
| 2007/0149988 A1 | 6/2007 | Michler et al. | |
| 2007/0149989 A1 | 6/2007 | Santilli et al. | |
| 2009/0088783 A1 | 4/2009 | Kennedy et al. | |
| 2009/0171380 A1 | 7/2009 | Whiting | |
| 2010/0211080 A1 | 8/2010 | Trivisani et al. | |
| 2011/0224700 A1* | 9/2011 | Schmidt | A61B 17/122 606/151 |
| 2011/0295291 A1* | 12/2011 | Trivisani | A61B 17/122 606/158 |
| 2012/0083803 A1 | 4/2012 | Patel et al. | |
| 2012/0226291 A1 | 9/2012 | Malizia et al. | |
| 2013/0245651 A1* | 9/2013 | Schmidt | A61B 17/122 606/157 |
| 2013/0253540 A1 | 9/2013 | Castro et al. | |
| 2013/0261642 A1 | 10/2013 | Willett et al. | |
| 2014/0054192 A1 | 2/2014 | Chancibot | |
| 2014/0142597 A1* | 5/2014 | Winkler | A61B 17/122 606/157 |
| 2014/0236170 A1* | 8/2014 | Kethman | A61B 17/1227 606/120 |
| 2014/0243862 A1* | 8/2014 | Bagaoisan | A61B 17/122 606/157 |
| 2014/0276970 A1 | 9/2014 | Messerly et al. | |
| 2016/0151073 A1 | 6/2016 | Castro et al. | |
| 2016/0354089 A1* | 12/2016 | Whiting | A61B 17/122 |
| 2017/0020530 A1 | 1/2017 | Willett et al. | |
| 2017/0027576 A1 | 2/2017 | Castro | |
| 2017/0209151 A1 | 7/2017 | Brown | |
| 2017/0238935 A1* | 8/2017 | Shi | A61B 17/1285 |
| 2017/0252042 A1 | 9/2017 | Kethman et al. | |
| 2018/0036008 A1 | 2/2018 | Ramsey et al. | |
| 2018/0168659 A1 | 6/2018 | Bagaoisan et al. | |
| 2018/0185029 A1 | 7/2018 | Lebens, III | |
| 2018/0228492 A1 | 8/2018 | Aranyi et al. | |
| 2018/0271527 A1 | 9/2018 | Shellenberger | |
| 2018/0271532 A1 | 9/2018 | Shellenberger | |
| 2018/0271535 A1 | 9/2018 | Shellenberger et al. | |
| 2018/0271536 A1 | 9/2018 | Shellenberger et al. | |
| 2019/0133590 A1 | 5/2019 | Richard | |
| 2019/0159782 A1 | 5/2019 | Kamaraj et al. | |
| 2019/0223874 A1 | 7/2019 | Pilletere et al. | |
| 2019/0314026 A1* | 10/2019 | Thomas | A61B 17/122 |

(56) References Cited

U.S. PATENT DOCUMENTS

| | | | |
|---|---|---|---|
| 2019/0314031 A1* | 10/2019 | Thomas | A61B 17/1227 |
| 2019/0321047 A1* | 10/2019 | Thomas | A61B 17/122 |
| 2020/0060684 A1* | 2/2020 | Thomas | A61B 17/122 |
| 2021/0052141 A1* | 2/2021 | Schurr | A61B 1/00101 |

FOREIGN PATENT DOCUMENTS

| | | |
|---|---|---|
| CN | 204839635 U | 12/2015 |
| CN | 106264647 A | 1/2017 |
| DE | 10116168 A1 | 11/2001 |
| DE | 202010008714 U1 | 12/2010 |
| EP | 0314064 A2 | 5/1989 |
| EP | 2074954 A1 | 7/2009 |
| EP | 3552560 A1 | 10/2019 |
| EP | 3572012 A1 | 11/2019 |
| GB | 2353710 A | 3/2001 |
| WO | 2013040306 A1 | 3/2013 |

OTHER PUBLICATIONS

U.S. Appl. No. 13/972,582, filed Aug. 21, 2013, inventor Manoj Patel.

U.S. Appl. No. 16/261,649, filed Jan. 30, 2019, inventor Justin Thomas, et al.

U.S. Appl. No. 16/261,662, filed Jan. 30, 2019, inventor Justin Thomas et al.

U.S. Appl. No. 16/261,803, filed Jan. 30, 2019, inventor, Justin Thomas, et al.

U.S. Appl. No. 16/364,648, filed Mar. 26, 2019, inventor, Roy J. Pilletere, et al.

U.S. Appl. No. 16/433,410, filed Jun. 6, 2019, inventor Justin Thomas, et al.

* cited by examiner

LIGATION CLIP WITH IMPROVED HINGE

CROSS-REFERENCE TO RELATED APPLICATION

This application claims the benefit of and priority to U.S. Provisional Patent Application No. 62/717,958 filed Aug. 13, 2018, the entire disclosure of which is incorporated by reference herein.

BACKGROUND

1. Technical Description

The present disclosure is directed to ligation clips for sealing body vessels and, more particularly, to ligation clips that have first and second legs joined together by a hinge.

2. Background of Related Art

Ligation clips are well known in the surgical arts and are commonly used during surgical procedures to ligate tissue, e.g., a body vessel. Ligation clips include first and second jaws that are coupled to each other by a hinge, e.g., a living hinge. Typically, the hinge is formed from inner and outer hinge portions and extends between proximal ends of the first and second jaws such that the ligation clip can pivot between open and clamped positions. Since the ligation clip has first and second jaws that can pivot between the open and clamped positions, the ligation clip can be compressed to facilitate passage through a small diameter cannula, subsequently opened to allow the ligation clip to be positioned about tissue, and clamped to ligate the tissue.

When known ligation clips are repeatedly moved between the open and clamped positions, stress or strain in the hinge of the ligation clip may cause the ligation clip to crack or fracture. It is important that the hinge be configured to facilitate repeated movement of the ligation clip between the open and clamped positions to allow the clip to remain structurally sound during insertion of the ligation clip through a trocar and placement about tissue.

A continuing need exists in the art for a ligation clip with an improved hinge that allows for repeated movement of the ligation clip between open and clamped positions while reducing the likelihood that the hinge will fracture.

SUMMARY

One aspect of the present disclosure is directed to a ligation clip including a first jaw, a second jaw, and a hinge. The first jaw includes a body having an inner surface defining a first clamping surface, and an outer surface. The second jaw includes a body having an inner surface defining a second clamping surface, and an outer surface. The hinge is integrally formed with the first and second jaws and includes an inner hinge portion and an outer hinge portion. The inner hinge portion has an inner surface that is contiguous with the first and second clamping surfaces of the first and second jaws, and an outer surface. The hinge is configured to facilitate pivotal movement of the first jaw in relation to the second jaw between an open position and a clamped position. The inner surface of the inner hinge portion is defined by a plurality of curved sections.

In embodiments, the plurality of curved sections includes a concave section and two convex sections.

In some embodiments, the concave section is bounded by the two convex sections.

In certain embodiments, the outer surface of the inner hinge includes a central convex section that is bounded by two concave sections.

In embodiments, the inner hinge portion has a thickness that is uniform between the two convex sections.

In some embodiments, the outer hinge portion includes an inner surface and an outer surface, wherein the inner surface of the outer hinge portion and the outer surface of the inner hinge portion define a cavity in the hinge.

In certain embodiments, the outer surface of the outer hinge portion includes a central concave section that is bounded by two convex sections.

In embodiments, the first jaw includes a longitudinal rib having a tissue engaging surface that is positioned in opposition to the second clamping surface of the second jaw when the ligation clip is in the clamped position.

In some embodiments, the second jaw has a first row of protrusions supported on one side of the second clamping surface and a second row of protrusions supported on an opposite side of the second clamping surface, wherein each of the protrusions of the first and second rows of protrusions has an inner side wall in opposition to a side wall of the longitudinal rib when the ligation clip is in the clamped position.

In certain embodiments, the inner side wall of each of the protrusions of the first and second rows of protrusions is angled towards the second clamping surface.

In embodiments, the first row of protrusions is laterally spaced from the second row of protrusions to define a channel that extends longitudinally between the first and second rows of protrusions, wherein the channel is positioned and configured to receive the longitudinal rib when the ligation clip is in the clamped position.

In some embodiments, the protrusions in the first row of protrusions are longitudinally aligned and spaced from each other and the protrusions in the second row of protrusions are longitudinally aligned and spaced from each other.

In certain embodiments, each of the protrusions in the first row of protrusions is longitudinally offset from the protrusions in the second row of protrusions such that the protrusions in the first and second rows of protrusions are alternatingly positioned on opposite sides of the second clamping surface along at least a portion of the length of the second clamping surface.

In embodiments, the first jaw includes a first locking element and the second jaw includes a second locking element, wherein the first locking element is movable into engagement with the second locking element to retain the ligation clip in the clamped position.

In some embodiments, the first locking element includes a hooked portion that extends downwardly and proximally from the first tissue clamping surface and the second locking element is configured to engage the hooked portion.

In certain embodiments, the second locking element defines a cam surface that engages the hooked portion to bias the hooked portion outwardly of the second locking element such that the hooked portion resiliently returns to an unbiased state after passing over the second locking element to position the hooked portion in contact with the engagement surface.

In embodiments, the ligation clip is formed of a polymeric material.

In some embodiments, the second jaw includes a distal portion including spaced teeth that are configured to engage tissue.

In certain embodiments, each of the spaced teeth has an apex that is configured to grip and stretch tissue as the ligation clip is moved to the clamped position.

In embodiments, the second jaw includes a spring arm that is positioned to engage and be deflected by the first locking element as the ligation clip is moved from the open position to the clamped position to urge the first and second locking elements to a latched position.

BRIEF DESCRIPTION OF THE DRAWINGS

Various exemplary embodiments of the presently disclosed ligation clip are described herein below with reference to the drawings, wherein.

DETAILED DESCRIPTION OF EMBODIMENTS

The presently disclosed ligation clip will now be described in detail with reference to the drawings in which like reference numerals designate identical or corresponding elements in each of the several views. It is to be understood that the disclosed embodiments are merely exemplary of the disclosure and may be embodied in various forms. Well-known functions or constructions are not described in detail to avoid obscuring the present disclosure in unnecessary detail. Specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

Figure 1:
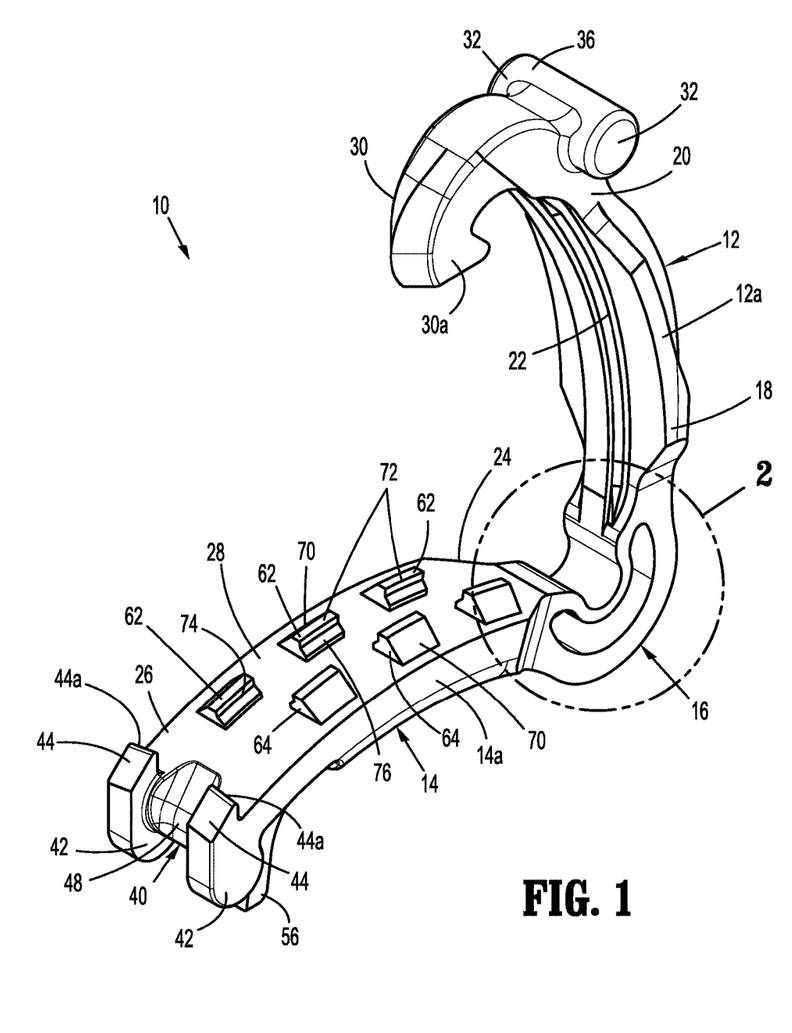
FIG. 1 is a side perspective view from a distal end of an exemplary embodiment of the presently disclosed ligation clip in an open position.
Figure 2:
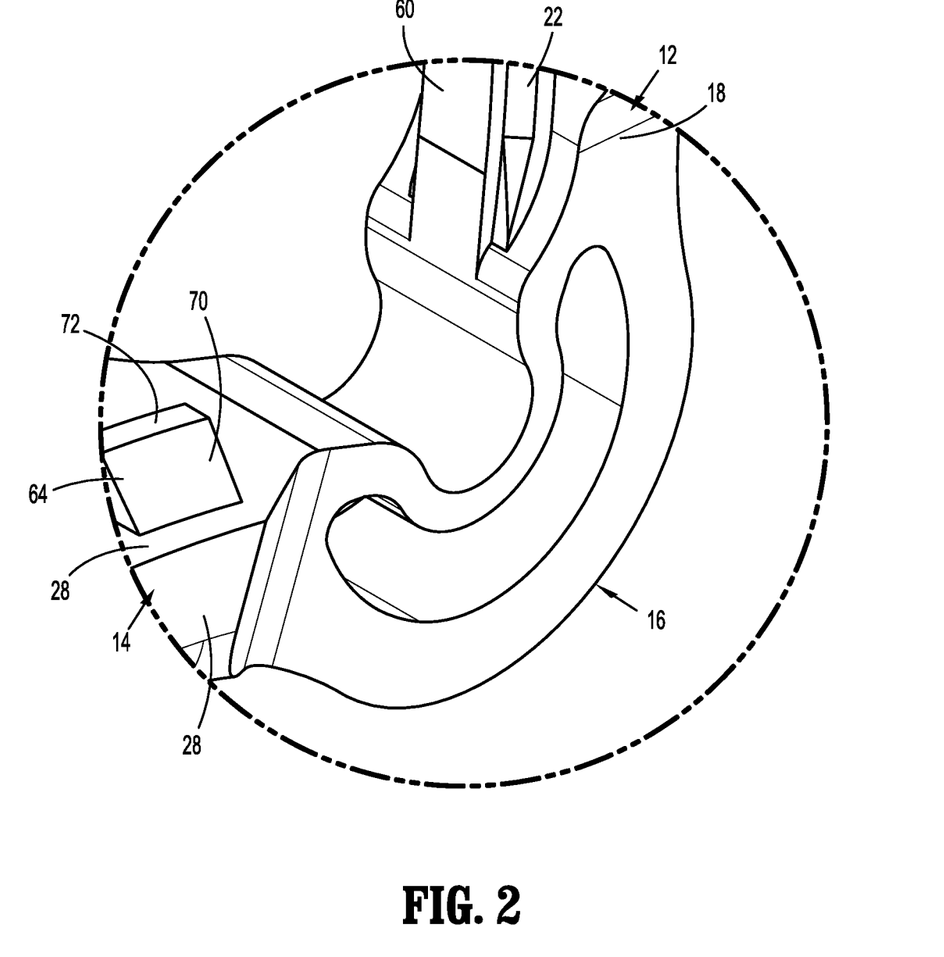
FIG. 2 is an enlarged view of the indicated area of detail shown in FIG. 1
Figure 3:
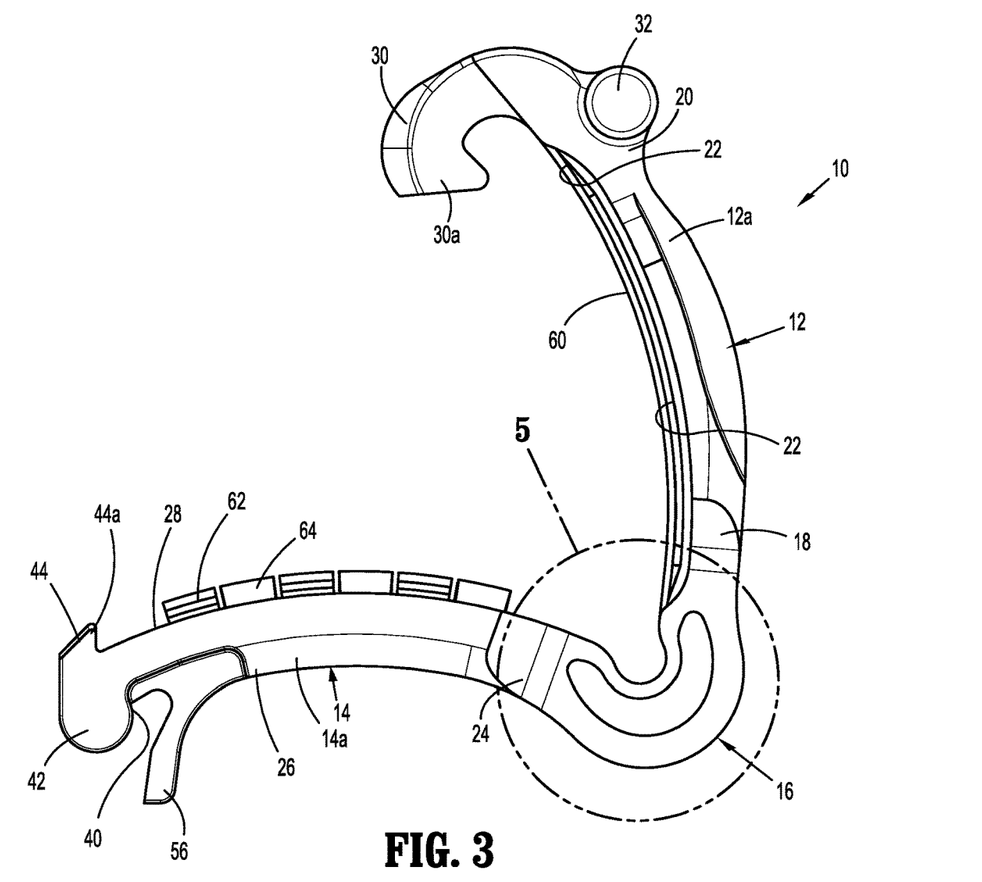
FIG. 3 is side view of the ligation clip shown in FIG. 1 in the open position.
Figure 4:
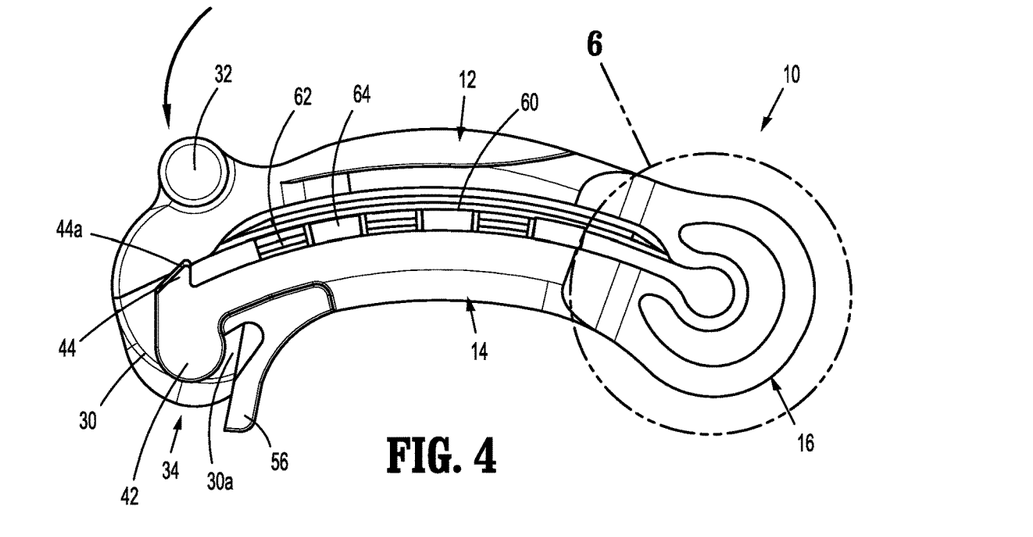
FIG. 4 is side view of the ligation clip shown in FIG. 3 in the clamped position.
Figure 4A:
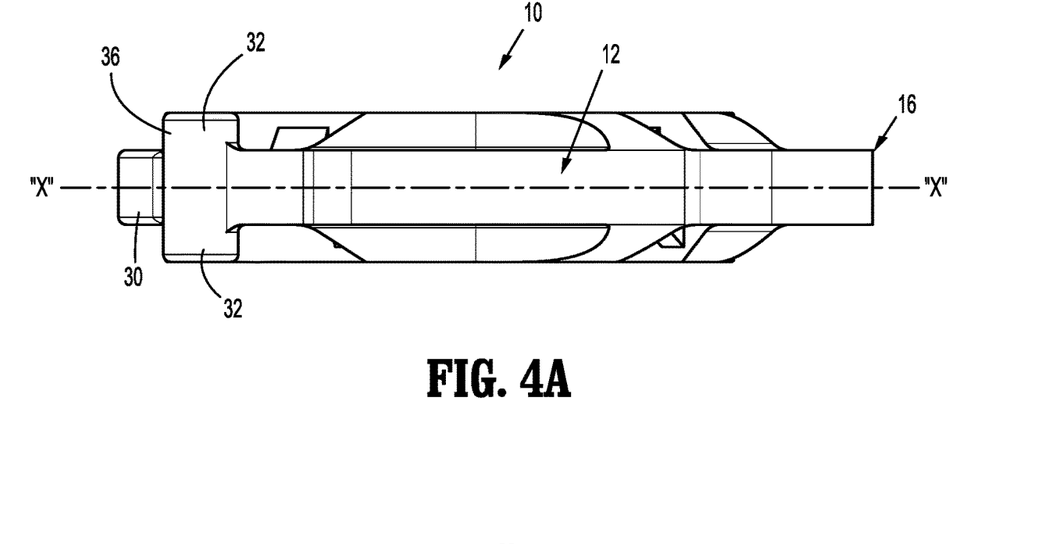
FIG. 4A is a top view of the ligation clip shown in FIG. 4 in the clamped position.

Referring to FIGS. 1-4A, an exemplary embodiment of the presently disclosed ligation clip is shown generally as ligation clip 10. The ligation clip 10 includes a first jaw 12, a second jaw 14, and a hinge 16 coupling the first jaw 12 to the second jaw 14. The first jaw 12 is pivotable in relation to the second jaw 14 about the hinge 16 to move the ligation clip 10 between an open position (FIG. 1) and a clamped position (FIG. 4). In the clamped position, the first and second jaws 12, 14 define a longitudinal axis "X" (FIG. 4A). In embodiments, the first and second jaws 12, 14 are curved along the longitudinal axis (FIG. 4) although other jaw configurations are envisioned. In embodiments, the hinge 16 is a living hinge that is integrally formed with proximal portions of the first and second jaws 12, 14.

The first jaw 12 has a body 12a having a proximal portion 18, a distal portion 20, and a clamping surface 22. The second jaw 14 has a body 14a having a proximal portion 24, a distal portion 26, and a clamping surface 28. The proximal portions 18, 24 of the first and second jaws 12, 14, respectively, are coupled to the hinge 16 such that the ligation clip 10 can pivot between the open position (FIG. 1) and the clamped position (FIG. 4). The distal portion 20 of the first jaw 12 includes a first locking element 30 and spaced bosses 32. The first locking element 30 includes a hooked portion 30a that extends downwardly and proximally from the tissue clamping surface 22 to define a portion of a latching mechanism 34 (FIG. 4) that is configured to retain the ligation clip 10 in the clamped position as described in further detail below.

Each of the spaced bosses 32 of the first jaw 12 extends outwardly of the body 12a. In embodiments, the spaced bosses 32 are integrally formed as a single transverse member 36 (FIG. 1) that is supported on the distal portion 20 of the first jaw 12. The transverse member 36 can be cylindrical although other configurations are envisioned. The bosses 32 extend outwardly from the body 12a of the first jaw 12 and are positioned and configured to be received within slots (not shown) formed in jaws of a clip applicator (not shown) to retain the ligation clip 10 on the clip applicator.

The second jaw 14 includes a body 14a. The distal portion 26 of the body 14a of the second jaw 14 includes a second locking element 40, spaced bosses 42, and spaced teeth 44. The spaced teeth 44 are configured to engage and/or penetrate tissue. In embodiments, each of the teeth 44 has an apex or pointed end 44a that grips and stretches tissue as the ligation clip 10 is moved from the open position (FIG. 1) towards the clamped position (FIG. 4) to improve the ligating characteristics of the ligation clip 10. The second locking element 40 defines a cam surface 48 (FIG. 1) that is configured to receive and guide the first locking element 30 into locking engagement with the second locking element 40 when the ligation clip 10 is moved to the clamped position (FIG. 4) to secure the ligation clip 10 in the clamped position. In particular, the cam surface 48 is configured to deflect the first locking element 30 outwardly in a distal direction as the first locking element 30 passes over the cam surface 48 such that when the first locking element 30 moves past the cam surface 48, the first locking element 30 resiliently moves into engagement with the second locking element 40.

The bosses 42 of the second jaw 14 are similar to the bosses 32 of the first jaw 12. More specifically, each of the spaced bosses 42 extends outwardly of the body 14a of the second jaw 14 and is positioned to be received within slots (not shown) formed in jaws of a clip applicator (not shown) to retain the ligation clip 10 on the clip applicator.

The second jaw 14 includes a spring arm 56 that is positioned to engage the first locking element 30 when the ligation element 10 is moved to the clamped position to retain the first locking element 30 and the second locking element 40 in the latched position (FIG. 4). The spring arm 56 is positioned to engage and be deflected by the first locking element 30 to create a compressive force within the spring arm 56 that presses against the second locking element 40.

In embodiments, each of the first and second clamping surfaces 22, 28 of the first and second jaws 12, 14, respectively, can include tissue retaining structure that is configured to prevent the ligation clip 10 from sliding along tissue while the ligation clip 10 is in the clamped position about the tissue. In embodiments, the clamping surface 22 of the first jaw 12 may include a longitudinal rib 60 that extends along all or a portion of the length of the clamping surface 22. In embodiments, the second clamping surface 28 of the second jaw 14 may also include a series of first protrusions 62 that are positioned along one side of the clamping surface 28 of the second jaw 14 and a series of second protrusions 64 that are formed along an opposite side of the second clamping surface 28 of the second jaw 14. In some embodiments, the first protrusions 62 are spaced from the second protrusions 64 to define an unobstructed channel that receives the longitudinal rib 60 when the ligation clip 10 is in the clamped position. In embodiments, the protrusions 62, 64 have an angled outer wall 70 (FIG. 2), a flat top wall 72, and an inner wall having a vertical portion 74, and a tapered portion 76. In certain embodiments, the first protrusions 62 are axially offset from the second protrusions 64 such that the first and second protrusions 62, 64 are alternatingly positioned along the longitudinal length of the second clamping surface 28.

Figure 5:
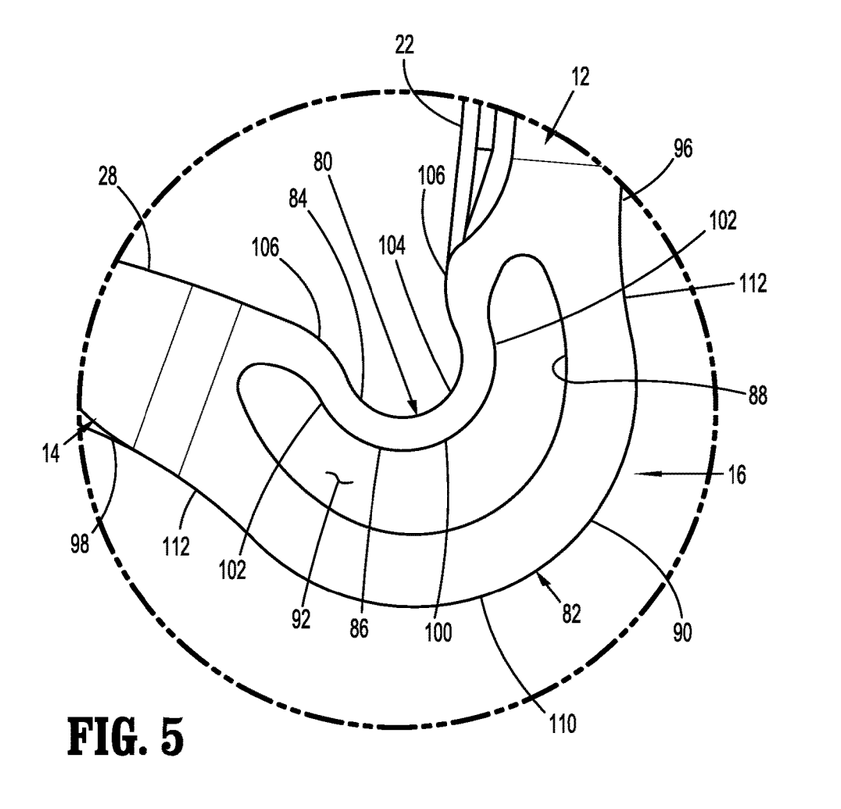
FIG. 5 is an enlarged view of the indicated area of detail shown in FIG. 3.
Figure 6:
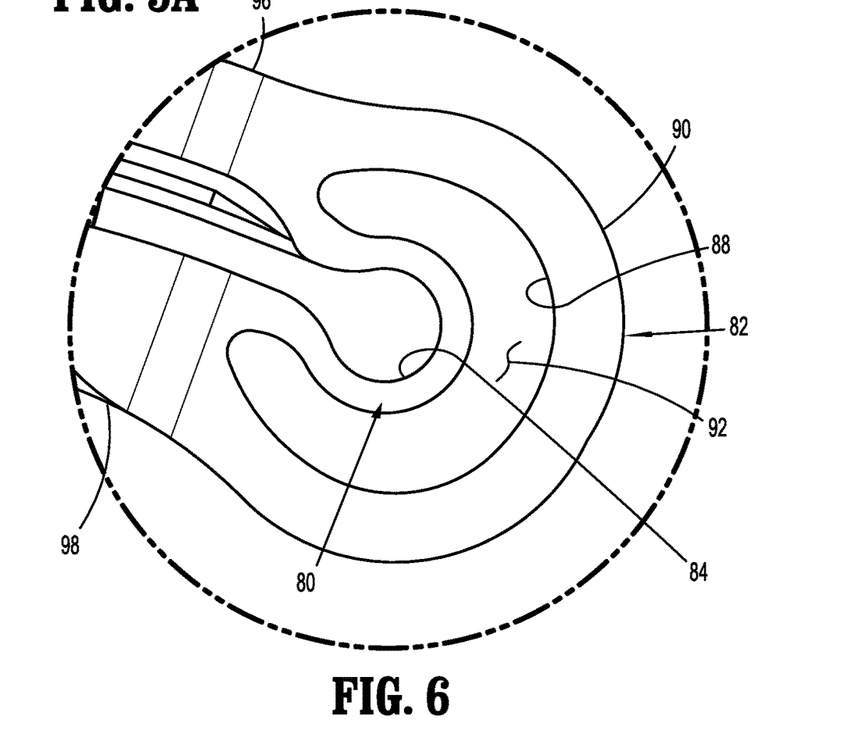
FIG. 6 is an enlarged view of the indicated area of detail shown in FIG. 4.

Referring to FIGS. 5-6, the hinge 16 includes an inner hinge portion 80 and an outer hinge portion 82. The inner hinge portion 80 includes an inner surface 84 that is contiguous with the first and second clamping surfaces 22, 28 of the first and second jaws 12, 14, respectively, and an outer surface 86. The outer hinge portion 82 includes an inner surface 88 and an outer surface 90. The outer surface 86 of the inner hinge portion 80 and the inner surface 88 of the outer hinge portion 82 define a cavity 92 within the hinge 16. The outer surface 90 of the outer hinge portion 82 is contiguous with outer surfaces 96, 98 of the first and second jaws 12, 14 of the ligation clip 10.

In the open position of the ligation clip 10 (FIG. 5), the outer surface 86 of the inner hinge portion 80 includes a plurality of different curved sections. More specifically, the outer surface 86 of the inner hinge portion 80 includes a central convex section 100 that is bounded by concave sections 102. Similarly, the inner surface 84 of the inner hinge portion 80 includes a plurality of curved sections including a central concave section 104 that is bounded by convex sections 106. In embodiments, the convex sections 106 are contiguous with the clamping surfaces 22, 28 of the first and second jaws 12, 14 of the ligation clip 10. In some embodiments, the inner hinge portion 80 has a substantially uniform thickness between the concave sections 102 and the convex sections 106 of the inner hinge portion 80.

In the open position of the ligation clip 10, the outer surface 90 of the outer hinge portion 82 also defines a convex section 110 that is bounded by less pronounced concave sections 112. In contrast, the inner surface 88 of the outer hinge portion 82 defines a single arcuate surface.

Figure 5A:
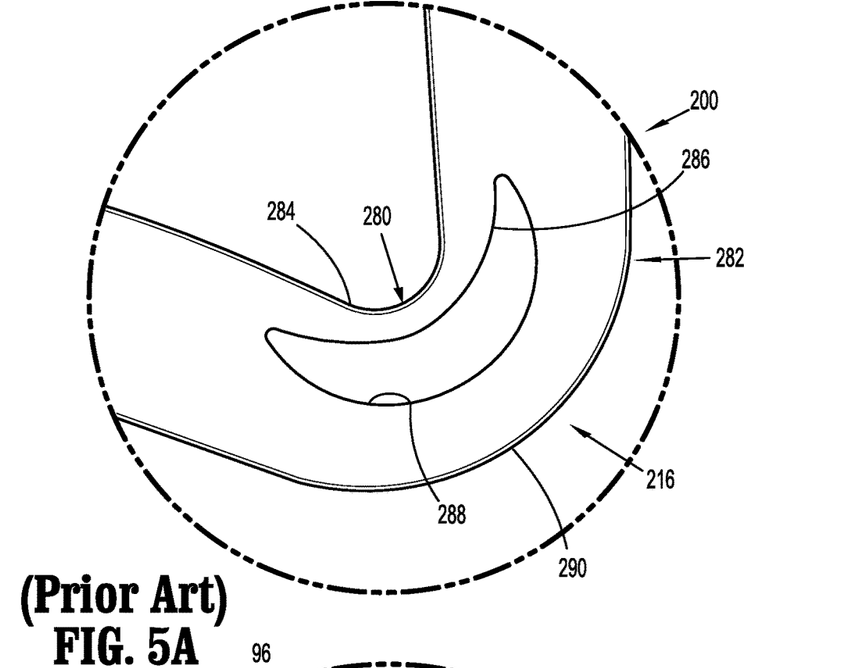
FIG. 5A is an enlarged view of a hinge of a Prior Art ligation clip.

Referring to FIG. 5A, in contrast to the hinge 16 of the presently disclosed ligation clip 10, the hinge 216 of known ligation clips 200 includes an inner hinge portion 280 that has inner and outer surfaces 284, 286 that define a single arc or curved surface. The hinge 216 also includes an outer hinge portion 282 that has inner and outer surfaces 288, 290 that define a single arc or curved surface.

Referring to FIG. 6, when the ligation clip 10 is moved to the clamped position, the configuration of the inner hinge 80 and to a lesser extent, the outer hinge portion 82, reduces the stress or strain in the hinge 16 as the ligation clip 10 is moved between the open and clamped position as compared to the stress or strain in known ligation clips, e.g., clip 200. As such, the ligation clip 10 is more capable of repeated movement between the open position and the clamped positions without fracturing and/or comprising the structural integrity of the ligation clip 10.

In embodiments, the surgical ligation clip 10 may be made, in whole or in part, of a resilient bioabsorbable and/or biocompatible polymeric material. Examples of suitable bioabsorbable and/or biocompatible polymers include acetal polyoxymethylene (POM), polyethylene terephthalate (PET), polybutylene terephthalate (PBT), polyoxymethylene, polyetheretherketone (PEEK), polypropylene, and polyethylene or other thermoplastic materials having similar properties that can be injection-molded. The clip may also be made of a polymer material or materials in combination with radiolucent metal alloys. Alternately, other materials may be used to form the clip 10 including biocompatible metals, plastics and composites.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A ligation clip comprising:
    a first jaw including a body having an inner surface defining a first clamping surface and an outer surface;
    a second jaw including a body having an inner surface defining a second clamping surface and an outer surface; and
    a hinge integrally formed with the first and second jaws, the hinge including an inner hinge portion and an outer hinge portion, the inner hinge portion having an inner surface that is contiguous with the first and second clamping surfaces of the first and second jaws and an outer surface, the hinge being configured to facilitate pivotal movement of the first jaw in relation to the second jaw between an open position and a clamped position;
    wherein the inner surface of the inner hinge portion is defined by a plurality of curved sections including a concave section and two convex sections, the concave section being bounded by the two convex sections, and wherein the outer surface of the inner hinge portion includes a central convex section that is bounded by two concave sections, the central convex section of the outer surface being aligned with the concave section of the inner surface and each of the two concave sections of the outer surface being aligned with a respective one of the two convex sections of the inner surface.

2. The ligation clip of claim 1, wherein the inner hinge portion has a thickness that is uniform between the two convex sections.

3. The ligation clip of claim 1, wherein the outer hinge portion includes an inner surface and an outer surface, the inner surface of the outer hinge portion and the outer surface of the inner hinge portion defining a cavity in the hinge.

4. The ligation clip of claim 3, wherein the outer surface of the outer hinge portion includes a central convex section that is bounded by two concave sections.

5. The ligation clip of claim 1, wherein the first jaw includes a longitudinal rib having a tissue engaging surface that is positioned in opposition to the second clamping surface of the second jaw when the ligation clip is in the clamped position.

6. The ligation clip of claim 5, wherein the second jaw has a first row of protrusions supported on one side of the second clamping surface and a second row of protrusions supported on an opposite side of the second clamping surface, each of the protrusions of the first and second rows of protrusions having an inner side wall in opposition to the longitudinal rib when the ligation clip is in the clamped position.

7. The ligation clip of claim 6, wherein the inner side wall of each of the protrusions of the first and second rows of protrusions is angled towards the second clamping surface.

8. The ligation clip of claim 7, wherein the first row of protrusions is laterally spaced from the second row of protrusions to define a channel that extends longitudinally between the first and second rows of protrusions, the channel being positioned to receive the longitudinal rib when the ligation clip is in the clamped position.

9. The ligation clip of claim 6, wherein the protrusions in the first row of protrusions are longitudinally aligned and spaced from each other and the protrusions in the second row of protrusions are longitudinally aligned and spaced from each other.

10. The ligation clip of claim 9, wherein each of the protrusions in the first row of protrusions is longitudinally offset from the protrusions in the second row of protrusions such that the protrusions in the first and second rows of protrusions are alternatingly positioned on opposite sides of the second clamping surface along at least a portion of the length of the second clamping surface.

11. The ligation clip of claim 1, wherein the first jaw includes a first locking element and the second jaw includes a second locking element, the first locking element being movable into engagement with the second locking element to retain the ligation clip in the clamped position.

12. The ligation clip of claim 11, wherein the first locking element includes a hooked portion that extends downwardly and proximally from the first clamping surface and the second locking element is configured to engage the hooked portion.

13. The ligation clip of claim 12, wherein the second locking element defines a cam surface that engages the hooked portion to bias the hooked portion outwardly of the second locking element such that the hooked portion resiliently returns to an unbiased state after passing over the second locking element to position the hooked portion in contact with the engagement surface.

14. The ligation clip of claim 1, wherein the ligation clip is formed of a polymeric material.

15. The ligation clip of claim 1, wherein the second jaw includes a distal portion, the distal portion including spaced teeth that are configured to engage tissue.

16. The ligation clip of claim 15, wherein each of the spaced teeth has an apex that is configured to grip and stretch tissue as the ligation clip is moved to the clamped position.

17. The ligation clip of claim 13, wherein the second jaw includes a spring arm that is positioned to engage and be deflected by the first locking element as the ligation clip is moved from the open position to the clamped position, the spring arm being positioned to urge the first and second locking elements to a latched position.

\* \* \* \* \*